(12) United States Patent  
Garcia Rubio

(10) Patent No.: US 8,717,554 B2  
(45) Date of Patent: May 6, 2014

(54) PHOTOELECTRIC METER FOR STAMPS PERFORATIONS

(76) Inventor: Claudio Garcia Rubio, Madrid (ES)

( * ) Notice: Subject to any disclaimer, the term of this patent is extended or adjusted under 35 U.S.C. 154(b) by 0 days.

(21) Appl. No.: 13/599,662

(22) Filed: Aug. 30, 2012

(65) Prior Publication Data

US 2013/0057853 A1 Mar. 7, 2013

(30) Foreign Application Priority Data

Aug. 31, 2011 (ES) .................................. 201100966

(51) Int. Cl.
*G01J 1/42* (2006.01)
(52) U.S. Cl.
USPC .......................................... 356/218; 356/213
(58) Field of Classification Search
USPC ........................ 356/213–218; 250/233 R, 555
See application file for complete search history.

(56) References Cited

U.S. PATENT DOCUMENTS

| | | | | |
|---|---|---|---|---|
| 3,692,298 A | * | 9/1972 | Peacock | 270/12 |
| 3,780,310 A | * | 12/1973 | Hudler | 250/555 |
| 3,852,715 A | * | 12/1974 | Morimoto | 382/175 |
| 4,007,410 A | * | 2/1977 | Hashimoto et al. | 318/571 |
| 4,281,243 A | * | 7/1981 | Hudler | 250/223 R |
| 4,637,523 A | * | 1/1987 | Levasseur | 221/13 |
| 5,019,695 A | * | 5/1991 | Itako | 235/434 |
| 6,591,251 B1 | * | 7/2003 | Leon et al. | 705/60 |

FOREIGN PATENT DOCUMENTS

| | | |
|---|---|---|
| ES | 02514118 | 6/1980 |
| GB | 190407653 | 0/1905 |
| GB | 468448 | 6/1937 |
| GB | 4811117 | 4/1938 |
| GB | 1355781 | 6/1974 |
| GB | 2022817 | 12/1979 |
| JP | 0830785 | 2/1996 |

OTHER PUBLICATIONS

Spanish Office of Patents and Trademarks; ES application P 201100966; listing of cited references; Jun. 2, 2013; 1 page.
"Perforation Gauges, PERFOtronic, The Optic-Electronic Perforation Gauger and Performeter and D Software", Document online: http://mdcstamps.com/safe-perforation-gauges.htm; copyright 2004-2013, Oct. 9, 2013; 4 Pages.

* cited by examiner

*Primary Examiner* — Sang Nguyen
(74) *Attorney, Agent, or Firm* — Stolowitz Ford Cowger LLP

(57) ABSTRACT

Photoelectric Meter for Stamps Perforations made up of two rows of photoreceptor cells conveniently connected to printed circuits endowed with a CICounter, a CIConverter and a Display, integrated within a single unit. This device allows measuring the horizontal as well as the vertical perforation of any stamp as well as the number of perforations and/or their variation in the superficial element to be measured, discriminating the type of perforation, of foot, of line, etc.

6 Claims, 2 Drawing Sheets

PHOTOELECTRIC METER FOR STAMPS PERFORATIONS

RELATED APPLICATIONS

This application claims priority to Spanish Application No. P201100966, filed on Aug. 31, 2011, which is incorporated herein in its entirety by reference.

BACKGROUND

In the world of philately a frequent problem is the identification of the perforations on a stamp, the number of perforation along the two centimeters at the sides, sometimes with a difference between the vertical and the horizontal sides (as they can be different); this operation usually made over an important number of stamps is carried out by means of a number of rulers graduated to such purpose, a perforation gauge, that compares the horizontal (and vertical) sides with the most similar scale of the gauge, and by application of a repetition pattern finds a coincident scale, that would indicated the value perforated. It is a slow and burdensome and not very well defined procedure especially when dealing with a certain range of scales, in such a way that perforations of the order of 11, 111/4, 111/2, 113/4, turn out to be very difficult to differentiate up to the extent that there are catalogues of stamps that only distinguish up to half of the perforation points. There are other measuring instruments such as the digital perforation gauge which is difficult to handle as requires a digitized image of the stamp; or the electronic perforation gauge, also based on photographic procedures, which is extremely expensive.

DETAILED DESCRIPTION

To solve this problem we provide a postage stamp edge perforation photoelectric meter to measure perforations along the edges of a postage stamp (not shown), which essentially is based on the capacity of specific materials to react before the presence of light with the emission of electrons. Obviously, this same characteristic of the materials would allow us to also detect the absence of light. Since this process, which involves a discharge of electrons, may be measured and quantified, the photoelectric meter of perforations would take care of the measuring process. This process may be understood as a phenomenon where with the interposition of a screen with holes (i.e., the stamp being measured) the passage of light generates areas of light alternated with dark areas, where originally there were only areas of light. In the photoelectric meter the location of the photoreceptors in a continuous line two centimeters long, allows to interpret the semi-dark phases as the number of photoreceptors in ON (or OF) position, depending on the light received (more or less); the connection of each line of photoreceptors with a Circuit Integrated Meter (integrated circuit meter) or counter allows to quantify the phenomenon and the Circuit Integrated Converter (integrated circuit converter) or converter, connected with the former introduces the binary data corresponding to the number of photoreceptors in ON position (the difference with the total of each line would give us the number of photoreceptors in OFF), sending the information already standardized to a Display.

The arrangement of the photoreceptors in two lines with a single point of contact between both and forming an angle of ninety degrees allows, by duplicating the circuit, to obtain simultaneously the measure of the horizontal and the vertical perforations on the horizontal and vertical edges of the stamp.

Figure 1:
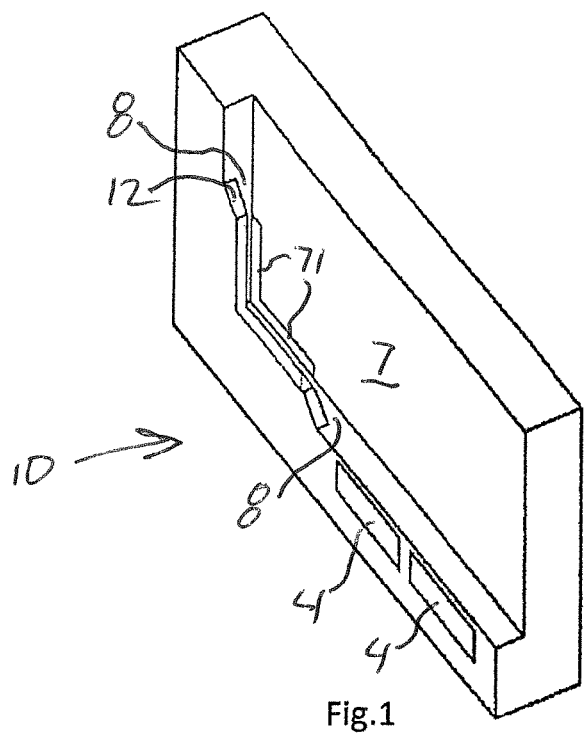
FIG. 1 depicts an example of a view in perspective of a Photoelectric Meter.
Figures 2, 3:
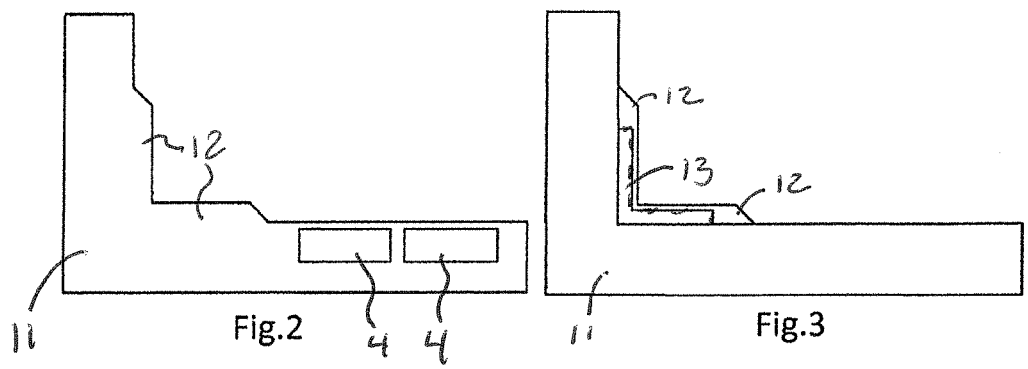
FIG. 2 depicts an example of a view in perspective of a Photoelectric Meter.
FIG. 3 depicts an example of a view in perspective of a Photoelectric Meter.
Figure 4:
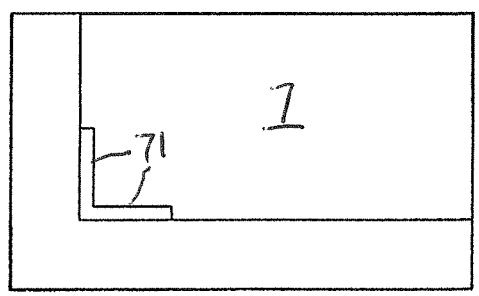
FIG. 4 depicts an example of a view in perspective of a Photoelectric Meter.

The photoelectric meter of postage stamp perforations will be now described by using an example and making reference to the attached drawings:

FIG. 1 represents an overall view in perspective of the photoelectric meter for postage stamp perforations 10. FIGS. 2, 3 and 4 show the vertical areas seen from the most external face 11 with a wall or lip 12 (FIG. 2), a base 7 to support the stamp (not shown) showing the symmetric L of the transparent material 71 (or any other opening) that may allow the passage of light (FIG. 4), and a reflecting element 13 (shown in dashed lines) positioned behind lip 12 and facing transparent material 71 (FIG. 3). Lip 12 may extend apart from base 7 by two millimeters and supports reflecting element 13 (FIG. 3), with an L-shape symmetrical to and facing the L-shape of the transparent material 71. The separation of lip 12 from base 7 is provided by a partition or wall 8 of perimeter contour which is shown in FIG. 1.

In operation, the stamp is placed over the base 7 represented by FIG. 4, keeping its horizontal and vertical sides in contact with the small perimeter wall 8, which will place the lower left corner of the stamp over the L-shaped window 71. Square lip 12, with the corresponding perimeter wall 8 closing makes a closed volume from where the light generated by the light transmitter (FIG. 5, element 5) is projected. Reflecting element 13 will be placed on the internal face of the lip 12 to facilitate the concentration of light towards the L-shaped window 71. The light goes through and is directed towards the transparent window 71 of the section represented by FIG. 4 behind which the lines of photoreceptors cells 1 are located. The stamp placed between the sections of FIGS. 3 and 4 prevents the light from going through allowing only the passage of light to the free spaces left by the empty perforations, overshadowing the rest. This new pre-distribution of light goes through the second transparent window in L 71 which is located in the section of FIG. 4 to impact on the two lines of photoreceptors 1, thus initiating the information processing that ends with the projection of the results on the corresponding screens 4 located in the right lower part of FIG. 5.

Figure 5:
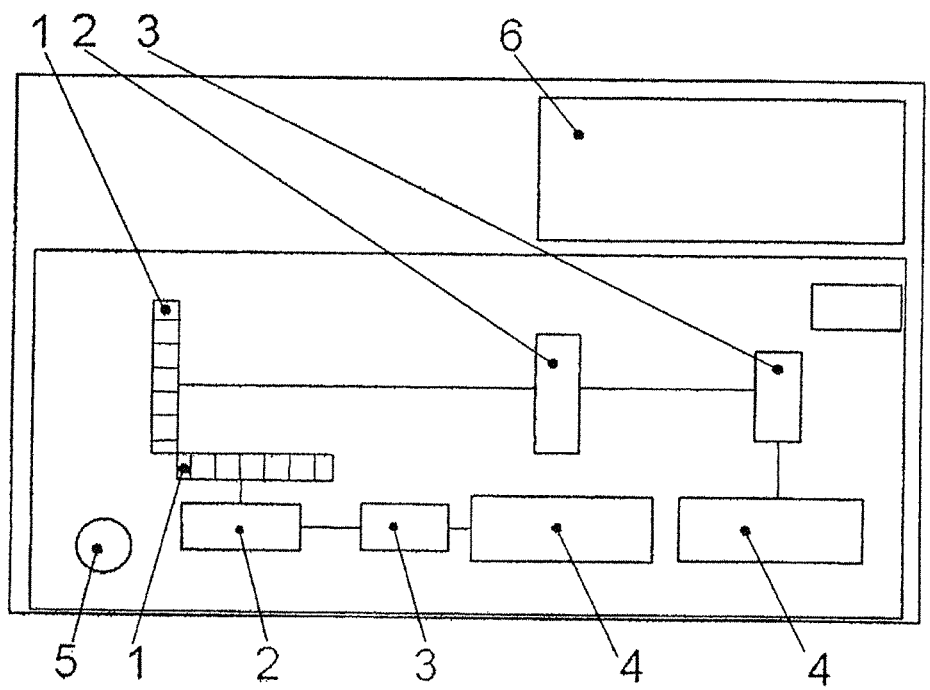
FIG. 5 depicts and example of a Photoelectric Meter.

FIG. 5 shows the photoelectric meter for stamp perforations 10 as a whole, basically consisting of two simple and identical plates of printed circuit made up by a Line of Photoreceptors 1, a Counter 2, a Converter 3 and finally a Screen 4; the several elements are connected in line and by this same order. Both plates will be conveniently embedded within the arrangement that will also be endowed with a simple light generator 5, a standard battery 6 and the elements required for an appropriate connection.

The light generating system may be practically of any kind although we propose a LED for its low consumption and durability. The line of photoreceptors 1 of two centimeters of length in total should preferably be made of square cells of half a millimeter by side and endowed with isolation capsules. This layout will guarantee sufficient sensibility for the perception of the smallest perforations in the market (the highest numbers being 17-18). The first counter will report the number of cells charged which will alternate with the same number of discharged cells. The second counter will translate—using a simple table of standardized lineal conversion—this information into a single figure, for example 14, that will appear on the information screen. Simultaneously the reading of the vertical side will take place, which will also be shown on its corresponding screen 4.

The invention claimed is:

1. A postage stamp edge perforation photoelectric meter, comprising:
    a base (7),
    an "L-shaped" window (71) that allows light from a light source to pass through the base and configured to align with perforations along adjacent perpendicular edges of one postage stamp, a wall (8) along the L-shaped window and a lip (12) extending from the wall apart from the base and configured to direct light to an "L-shaped" array of photoreceptor cells that are connected to a meter (2), a converter (3) and Screen (4) to provide detection and display of postal stamp edge perforation measurements.

2. The postage stamp edge perforation photoelectric meter of claim 1 further comprising a reflecting element that is supported by the lip and wherein the photoreceptor cells that are located behind the "L-shaped" window and the reflecting element is configured to direct light to photoreceptor cells.

3. The postage stamp edge perforation photoelectric meter of claim 2, wherein the reflecting element is positioned in the lip behind a window with transparent material.

4. The postage stamp edge perforation photoelectric meter of claim 2, wherein the reflecting element is "L-shaped" and the reflecting element and the "L-shaped" window are symmetrical and located opposite one another.

5. The postage stamp edge perforation photoelectric meter of claim 1, wherein the "L-shaped" window includes a transparent material.

6. The postage stamp edge perforation photoelectric meter of claim 1, wherein the photoreceptor cells are of a dimension of up to 0.5 mm to provide postal stamp edge perforation measurements.

* * * * *